United States Patent [19]

Ohmura et al.

[11] Patent Number: 5,028,664
[45] Date of Patent: Jul. 2, 1991

[54] DRUG-RELEASE CONTROLLING COATING MATERIAL FOR LONG ACTING FORMULATIONS

[75] Inventors: Tadayoshi Ohmura; Muneo Fukui; Hiroshi Sugiura; Satoru Yoneya; Toshiharu Hosono, all of Shizuoka; Atsushi Kajiyama, Saitama, all of Japan

[73] Assignee: Yamanouchi Pharmaceutical Co., Ltd., Tokyo, Japan

[21] Appl. No.: 490,831

[22] Filed: Mar. 8, 1990

[30] Foreign Application Priority Data

Mar. 10, 1989 [JP] Japan ................... 1-58684

[51] Int. Cl.$^5$ ............................. C08L 33/00
[52] U.S. Cl. ...................... 525/217; 525/221; 424/467; 424/480; 424/487; 424/497; 524/521
[58] Field of Search ............. 525/221, 217; 424/497, 424/467, 480, 487; 524/521

[56] References Cited

U.S. PATENT DOCUMENTS

| | | |
|---|---|---|
| 3,236,914 | 2/1966 | Murdock ............... 525/217 |
| 3,300,429 | 1/1967 | Glavis ................. 525/217 |
| 3,369,009 | 2/1968 | MacArthur ............ 525/217 |
| 3,641,237 | 9/1970 | Gould ................. 424/427 |
| 4,065,523 | 12/1977 | Hutton ................ 525/217 |
| 4,082,705 | 4/1978 | Beede ................. 525/217 |
| 4,339,373 | 7/1982 | Robinson .............. 525/221 |
| 4,539,199 | 9/1985 | Orbán ................. 424/480 |
| 4,830,911 | 5/1989 | Kojima ............... 428/474.4 |
| 4,855,363 | 8/1989 | Moteki ............... 525/221 |

Primary Examiner—Thurman Page
Assistant Examiner—William E. Benston
Attorney, Agent, or Firm—Burgess, Ryan & Wayne

[57] ABSTRACT

A coating material for controlling drug release, useful for long acting formulations—e.g. for once-a-day administration, and to a long acting granular composition comprising a drug (especially one conventionally difficult to prepare in long acting form) coated with the coating material. This composition may be mixed with other granular drug formulations. The drug-release controlling coating material comprising, in a specific ration, one specific water-insoluble and low water-permeability polymers and two materials differing from each other in the pH-dependency of their solubility (pH-dependent polymer-materials).

1 Claim, 7 Drawing Sheets

DRUG-RELEASE CONTROLLING COATING MATERIAL FOR LONG ACTING FORMULATIONS

BACKGROUND OF THE INVENTION

1. Field of the Invention

This invention relates to a coating material for controlling drug release, useful for long acting formulations e.g. for once-a-day administration, and to a long acting granular composition comprising a drug (especially one conventionally difficult to prepare in long acting form) coated with said coating material. This composition may be mixed with other granular drug formulations—e.g. of different maintenance and/or initial rate or delay of drug release such as granular semi-long acting pharmaceutical preparations and/or granular gastric juice-soluble pharmaceutical preparations.

2. Description of the Related Art and Problems to be solved

Long acting formulations have advantages for medical treatment, since the dosing frequency is decreased and this increases compliance with the prescribed dosing regime. Various types of formulation have been investigated in order to develop a long acting formulation. However, for many drugs it has not been easy to develop a sufficiently long acting formulation, especially one which gives effective drug concentration in the blood rapidly after administration and maintains constant drug concentration in the blood for a long time.

The residence time of orally administered drugs in the small intestine is about 2 to 6 hours, and absorption rate through the gastrointestinal tract varies greatly along the tract. Generally, drugs are poorly absorbed in the gastric portion, and are mainly absorbed in the small intestine. The drug absorption rate decreases in the order of duodenum, jejunum and ileum, and the drug is absorbed in the large intestine (specifically, colon) hardly at all or at a very low rate. Hence, in designing a long acting formulation, consideration must be given to the kind of drug and to the absorption characteristics of the gastrointestinal tract. Various methods have hitherto been investigated in attempts to solve such problems.

A typical example is a binary thermodynamic penetration device of Alza Corp. (Japan Kokai No. 41609 (1985)). The device provides a penetration chamber having a partition wall and composed of at least partially semipermeable material. The formed separated chambers contain first and second penetration compositions, respectively. A passageway passes through the chamber from the outside to the first penetration composition to send the drug outside. The device can continuously send out a definite amount of the drug at a desired site of the body and independent from the pH in the body (the 0 order release). However, drugs which are highly dependent on the properties of the absorption site or liable to be metabolized cannot be sufficiently absorbed by the 0 order release type long acting pharmaceutical preparations.

Nicridipine (generic name) hydrochloride is difficult to formulate as a long acting preparation, but we have previously obtained a somewhat long acting formulation (see unexamined Japanese Patent Publication No. Sho.58-116414) by coating small granular nuclei such as Nonpareil [trade name] with nicardipine hydrochloride, entero- and/or gastrosoluble base material and a surface active agent, and further coating the product with a drug-release controlling material such as Eudragit RL [trade name, made by Rohm and Haas Co., a 1 : 2 : 0.2 ethylacrylate/methylmethacrylate/trimethylammonio-ethylmethacrylate chloride copolymer]. This granular formulation has been put to practical use as a fairly long acting preparation for twice-a-day administration, but cannot be used satisfactorily for once-a-day administration. We have conducted various investigations for the purpose of obtaining a once-a-day oral administration-type formulation for drugs which are difficult to prepare in satisfactory long acting form, and have obtained a drug-release controlling coating material by mixing, in a specific ratio, specific water-insoluble and low water-permeability polymer [a] and at least two materials (usually polymers) [b] and [c] differing from each other in the pH-dependency of their solubility, namely, pH-dependent materials, (e.g. being soluble only at pH values above 6 and 7 respectively), and have discovered that the thus obtained drug-release controlling coating material unexpectedly can give excellent medicament-dissolution results.

All parts and percentages herein are by weight unless otherwise specified.

SUMMARY OF THE INVENTION

The present invention provides a drug-release controlling coating material consisting essentially of a] 60 parts to 85 parts of ethylacrylate/methylmethacrylate/ trimethylanmmonioethylmethacrylatechloride (1 2 0.1 molar ratio) copolymer, b] methylmethacrylate/methacrylic acid (1 : 1 molar ratio) copolymer, c] methylmethacrylate/methacrylic acid (2 : 1 molar ratio) copolymer, the total amount of the materials [b] and [c] being 15–40 parts, and optionally d] ethylacrylate/methylmethacrylate/trimethylammonioethylmethacrylatechloride (1 : 2 : 0.2 molar ratio) copolymer, in an amount of 0–30 parts per 100 parts of the total amount of the materials [a], [b] and [c].

DETAILED DESCRIPTION OF THE INVENTION

The drug-release rate of coating material of the present invention at pH 7.2 is 20–70% (preferably 30–50%) in 3 hours, and the coating material gives rapid drug-release after 3 hours, said rate at pH 7.5 is above 50% (preferably, above 70%) in 2 hours. The coating material of the present invention thus has ideal drug-release properties.

The above copolymer [a] is suitably a water-insoluble high molecular weight material (e.g. molecular weight about 150,000) having small to water. Suitable copolymer [a] is commercially available under trade name Eudragit RS (for example, Eudragit RS 100). The copolymers [b] and [c] are suitable high molecular weight materials (e.g. molecular weight about 135,000); they preferably differ in the pH-dependency of their solutions - e.g. copolymer [b] having solubility only at pH above 6.0 and copolymer [c] solubility only at pH above 7.0, the copolymers being insoluble or poorly soluble below these respective pH values. Suitable copolymers [b] and [c] are also commercially available under trade names Eudragit L (for example, Eudragit L 100) and Eudragit S (for example, Eudragit S 100) respectively, and are in practical use as entero-soluble base materials. The copolymer [d] is suitable a water-insoluble high-molecular weight material (e.g. molecular weight about 150,000) showing greater swelling and generation by water than copolymer [a]. Suitable copolymer [d] is commercially available under trade name Eudragit RL (for example, Eudragit RS 100L - former name: Eudragit RL 100).

The amount of [c] is preferably 0.4 to 2.3 times that of [b]. If desired, plasticizers, lubricants, flavouring materials, odorants, etc. (namely, the usual additives for conventional formulations) may added to the coating material of the present invention. The amount of such additives is, usually, less than 20%, preferably less than 10%.

As apparent from the dissolution test below (Test Example 1), a typical dissolution property of the drug-release controlling coating material of the present invention shows a low dissolution rate at pH 1.2 (about 5 to 20% in 3 hours); but at pH 7.2 this coating material has a controlled dissolution rate of 30 to 50% in 3 hours and has rapid dissolution character after 3 hours, and at pH 7.5 the dissolution rate is above 70% in 2 hours. Thus the coating material of the present invention has unique dissolution properties, so that drug-release is inhibited in the gastro tract, is moderate in a neutral pH range, and is rapid in the alkaline range (pH 7.2-7.8) - i.e. at such alkaline pH, a large amount of the drug is released in a short time.

A typical dissolution property is explained above, based on Test Example 1; but, the coating material of this invention is not always limited to one showing such typical dissolution property.

Thus, by the present invention, it has become possible to control drug release in different portions of the gastro-intestinal tract.

Drugs difficult to prepare in long acting form are termed herein "difficultly prolonged".

The drug-release controlling coating material of the invention is useful, preferably for preparing long-acting formulations of drugs which are difficultly prolonged because they have one or more of the following characteristics :

1] short biological half life (in blood);
2] absorbability varying along the-gastro-intestinal tract so as to impair long-lasting action;
3] sparingly soluble in the high pH range.

Examples of drugs having such characteristics are amosulalol, nicardipine, propranolol, diltiazem, nifedipine, isosorbide nitrate, cephalexin, etc.

A drug having the Characteristic [4] that it is sensitive to the first-pass effect in the liver, in addition to an above-mentioned characteristic [1], [2], or [3] is particularly difficult to prepare in long acting form and such drug is termed herein "very difficultly prolonged"; an example of such drug is nicardipine.

Hereinafter there are explained in greater detail long acting granular preparations formed by coating granules (or pellets) containing difficulty prolonged drug with a drug-release controlling coating material of the present invention, and also mixed granules or pellets comprising such a granular preparation and any other granular drug preparation(s)-the latter usually comprising less long acting and/or more rapid release material(s) to give a composite formulation providing overall a desirable initial and sustained drug release.

There is no particular restriction on the granules (or pellets) containing difficulty prolonged drug.

The granules or pellets according to the invention, dependent upon the nature the drug used, may also contain any of gastro-soluble base material, entero-soluble base material, organic acid, surface active agent, excipient, binder, etc.

For instance, when the drug is sparingly soluble in the alkaline range and its absorption rate in the lower part of the gastro-intestinal tract is low (for example, nicardipine hydrochloride), the granules or pellets are preferably formed by coating fine particle nuclei with the foregoing drug, enterosoluble base material and/or gastro-soluble base material, and surface active agent; and for another drug such as amosulalol hydrochloride, the granules or pellets preferably contain a pharmaceutically acceptable organic acid.

As entero-soluble base material for use as above, there are, for example, high molecular weight materials soluble at the pH in the intestines, examples being the beforementioned Eudragit L and Eudragit S as well as hydroxypropylmethyl cellulose phthalate, cellulose acetate phthalate, shellac, etc.

As gastro-soluble base materials for use as above, there are, for example, HPC (trade name, made by Nissan Chemical Industries Ltd., component: hydroxypropyl cellulose), Marcrogol (generic name of polyethylene glycol), Metholose (trade name, made by Shin-etsu Chemical Industry Co , Ltd., component: methyl cellulose), TC-5 (trade name, made by Shin-etsu Chemical Industry Co., Ltd., component: hydroxypropyl methylcellulose), etc.

Examples of the surface active agent are Tween 80 (trade name, made by Kao Atlas Co., component: polyoxyethylene sorbitan mono-oleate), Renex 30 (trade name, made by ICI PLC., component: polyoxyethylene alkyl ether), Nikkol HCO-60 (trade name, made by Nikko Chemicals Co., Ltd., component: polyoxyethylene hydrogenated castor oil), etc.

Examples of organic acids are citric acid, tartaric acid, etc.

The fine particle nuclei may be made from sucrose, crystalline cellulose, a mixture of sugar and corn starch, a mixture of crystalline cellulose and lactose, etc. Examples of the fine particle nuclei are Nonpareil (for example, 103) (trade name, made by Freund Sangyo K.K.) made from sucrose.

According to one embodiment of the present invention, a nicardipine granular long acting pharmaceutical preparation can be produced by the following method: [i] nicardipine or its salt and [ii] enteric base and/or gastric juice-soluble base and surface active agent are dissolved in an organic solvent; the obtained solution is spray coated on fine particle nuclei (e.g. by flow coating or fluidized layer coating) followed by drying; the dried granules or pellets are further sprayed with a solution containing drug release control substance according to the invention and plasticizer and dried.

Organic solvents such as methanol, ethanol, isopropanol, chloroform, acetone and methylene chloride can be used, singly or in combination.

Drying is preferably performed at low temperatures sufficient to vaporise and eliminate the organic solvent, such as at 40° C. for a few hours.

During the process nicardipine or its salt takes an amorphous form.

Plasticisers, for example, Macrogol (polyethylene glycol), Tween 80 (Kao Atlas Co., Ltd.; polyoxyethylene sorbitan monooleate), Triacetin (glyceryl triacetate) and triethyl citrate can be used.

Any type of conventional fillers, lubricants and binders can be used in the present invention without limitation.

Granules or pellets of amosulalol for a long acting pharmaceutical preparation can be produced by the following method:

[i] amosulalol or its salt and [ii] organic acid and filler are kneaded with an appropriate amount of water, granulated and dried. These qranules or pellets can be converted to a long-acting formulation by coating with a composition according to the invention.

The obtained granular long acting pharmaceutical preparations can be administered once daily alone or mixed with conventional granular semi-long acting pharmaceutical preparations and/or granular quick-release preparations to make a mixed long acting granule formation. The mixed granules are useful for drugs which have very short blood half life ($t_{\frac{1}{2}}$), poor solubility in alkaline conditions, and large first pass effect, and so are very difficultly prolonged.

A granular long acting pharmaceutical preparation of the present invention [I] can be mixed with granular semi-long acting pharmaceutical preparations [II] and/or granular gastric juice - soluble pharmaceutical preparations [III]. Examples of [II] and [III] are given in Japanese Patent Publication No.7047(1989) as round shaped granules. The granular semi-long acting pharmaceutical preparations given in this publication are: [i] fine particle nuclei coated with [a] drugs which are very difficultly prolonged such as amorphous nicardipine or its salts, and [b] one or more enteric bases selected from hydroxypropylmethylcelulosephthalate, methyl methacrylate/methacrylic acid copolymer, cellulose acetate phthalate and shellac, and/or one or more gastric juice soluble bases selected from hydroxypropylcellulose, polyethylene glycol, methylcellulose and hydroxypropylmethylcellulose, and one or more surface active agents selected from polyoxyethylenesorbitan monooleate, polyoxyethylene alkyl ether and polyoxyethylene hardened castor oil; and [ii] round shaped granular long acting pharmaceutical preparations produced by coating above coated nuclei [i] with one or more drug release control copolymers composed of ethyl acrylate, methylmethacrylate and trimethylammonioethylmethacrylate chloride and ethylcellulose The granules for gastric juice-soluble pharmaceutical preparations [III] are round shaped granules prepared by coating the fine particle nuclei with a drug which is very difficultly prolonged and gastric juice-soluble base. Appropriate ratios for combination of the above materials are, for example, in the case of mixing [I] and [II], 100 parts of [I] to 20–300, preferably 30–200, parts of granules [II]. Granules [III] may optionally be added, and in the case of combining [III], [III] is added in amounts of 5–30, preferably 5–25 parts per 100 parts of the total amount of the mixed granular preparation which may or may not contain [II]. The mixed granules preparation can provide a rapid elevation of concentration of the effective component in the blood and maintain the required concentration for 24 hours, and are therefore particularly preferable to provide a long acting pharmaceutical preparation with rapid manifestation of effect by one daily administration.

The drug release coating material of the present invention can also be applied to conventional tablets, granules and pellets to impart long acting properties.

The granular long acting pharmaceutical preparations of the present invention excellent drug releasing characteristics in dissolution tests using artificial digestive juice. Furthermore, suitable blood concentration pattern for use as a long acting pharmaceutical preparation was shown in the test using beagle dogs.

TEST EXAMPLE 1

Figure 1:
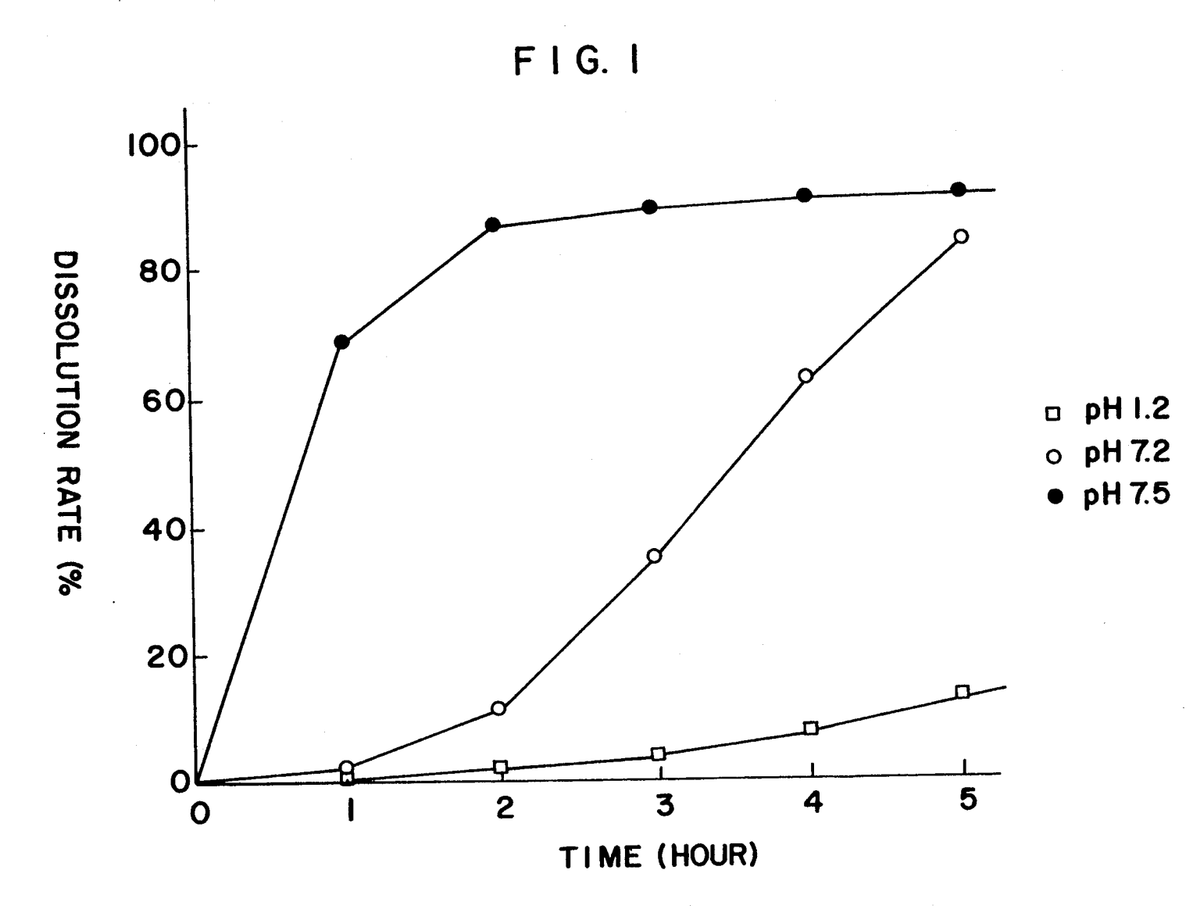
FIG. 1 and 2 shows the results of Test Example 1 dissolution test.
Figure 2:
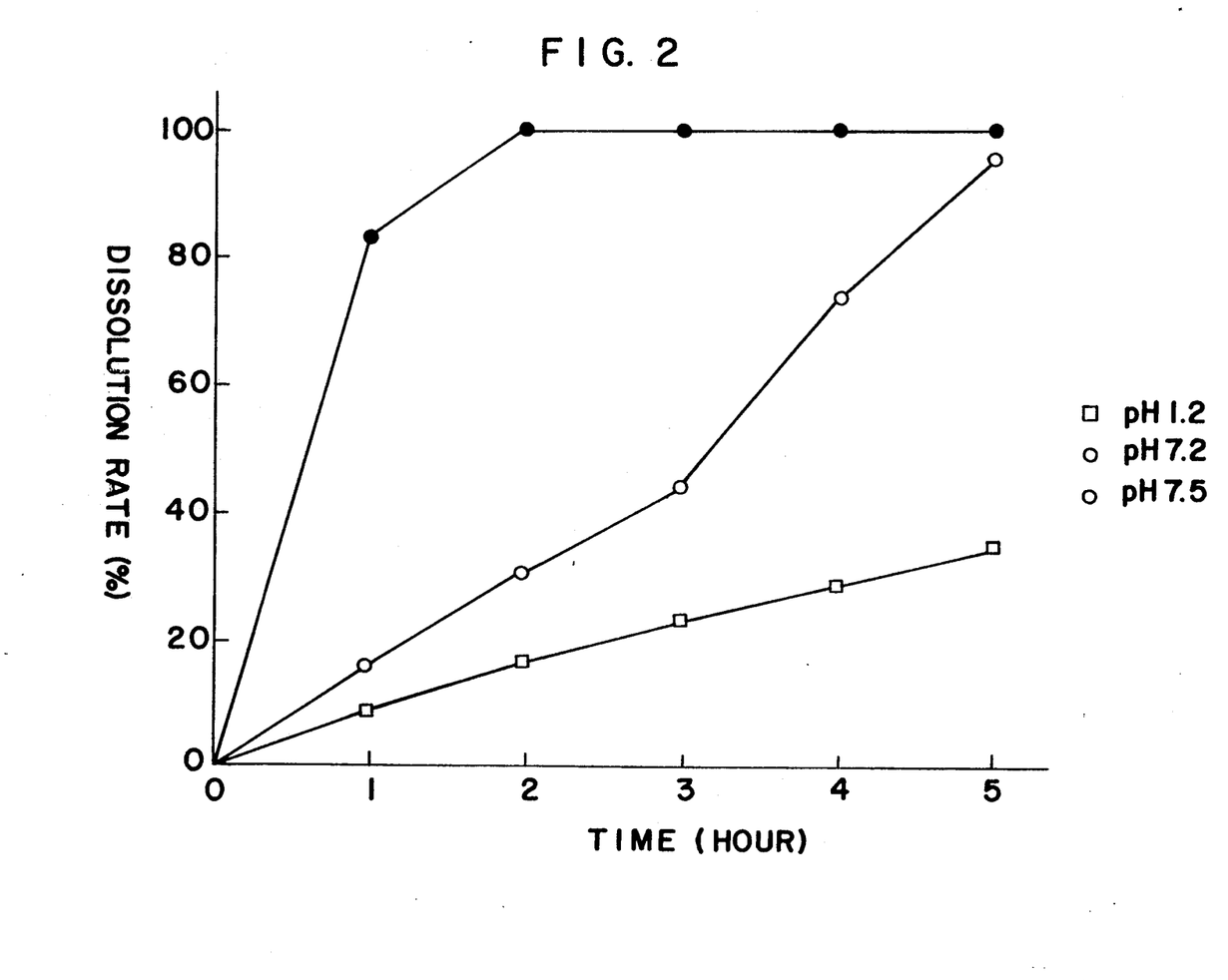

A dissolution test was performed with the release controlled pharmaceutical preparations of Examples 1 and 2. The test was performed according the general test method, dissolution test, Japanese Pharmacopeia XI. The 1st test solution (pH 1.2) and phosphate buffers (pH 7.2 and 7.5) were used as test solutions. The results are shown in FIG. 1 (pharmaceutical preparation of Example 1) and FIG. 2 (pharmaceutical preparation of Example 2), which clearly indicate that drug release was controlled at pH 7.2 or below, and was rapidly accelerated at pH 7.5.

TEST EXAMPLE 2.

Figure 3:
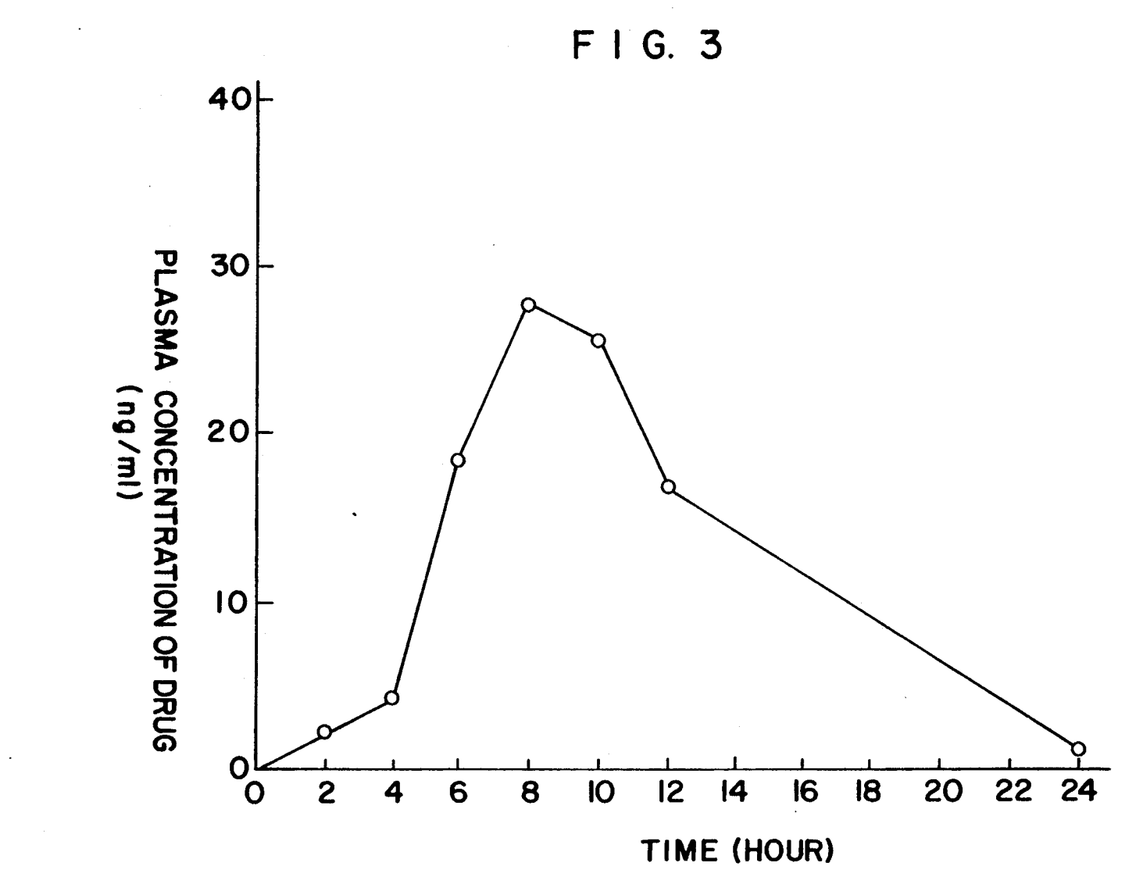
FIG. 3 shows the result of Test Example 2.

A long acting pharmaceutical preparation containing 100 mg of nicardipine hydrochloride prepared by Example 1 was orally administered with 20 ml of water to six male beagle dogs. After administration, blood was drawn at predetermined intervals and the plasma concentrations of nicardipine were determined. The results are shown in FIG. 3

TEST EXAMPLE 3

Figure 4:
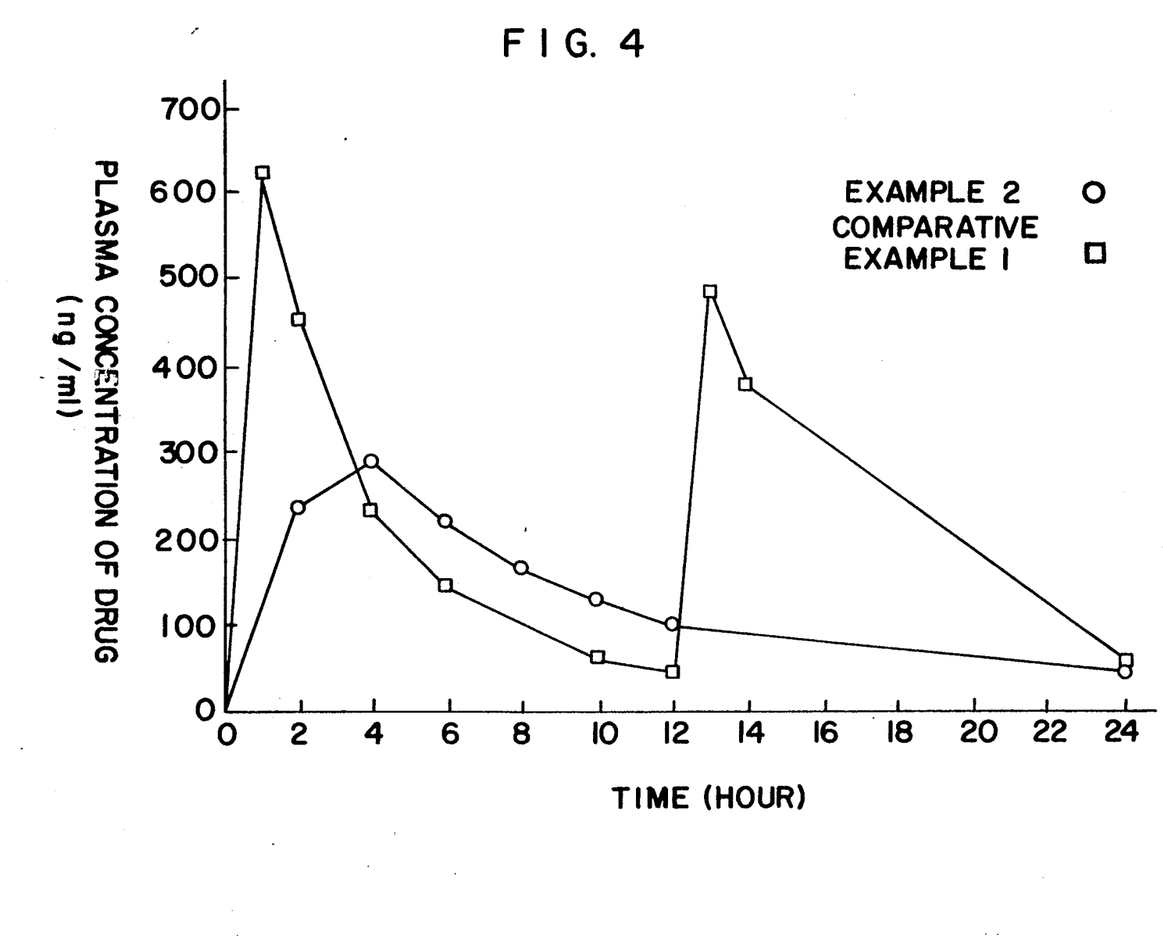
FIG. 4 shows the result of Test Example 3.

A long acting pharmaceutical preparation containing 100 mg of amosulalol hydrochloride prepared by Example 2 was administered once daily and one control tablet prepared by comparative example 1 containing 50 mg of amosulalol hydrochloride was administered twice daily to male beagle dogs. After administration, blood was drawn at predetermined intervals and the plasma concentrations of amosulalol were determined and compared. The results are shown in FIG. 4.

The conventional pharmaceutical preparation showed a rapid elevation of plasma concentration, while the preparation produced by Example 2 of the present invention showed a good slow releasing plasma concentration pattern.

TEST EXAMPLE 4

Figure 5:
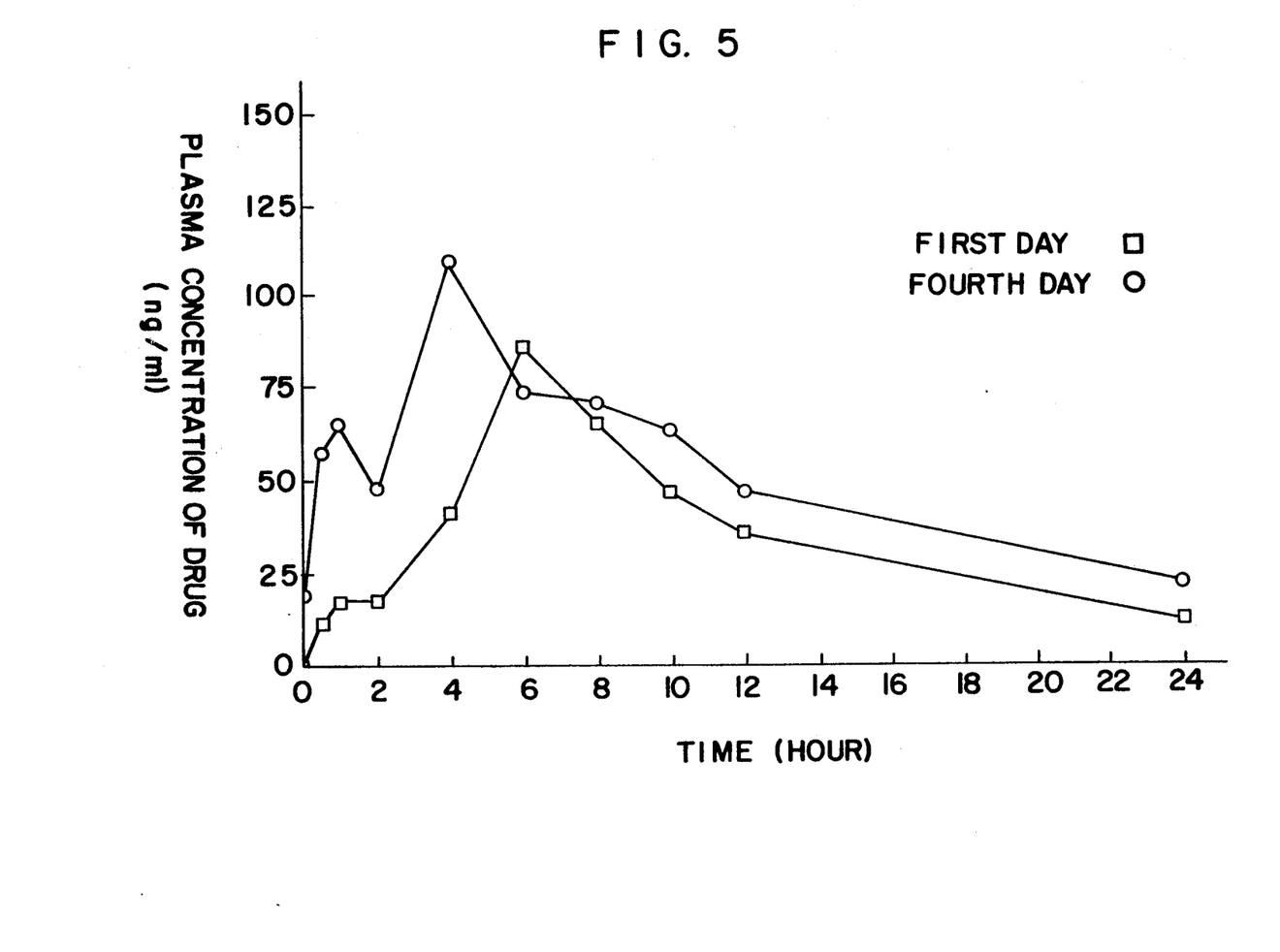
FIG. 5 shows the result of Test Example 4.

A long acting pharmaceutical preparation containing 200 mg of nicardipine hydrochloride prepared by Example 3 was administered once daily for four days to six male beagle dogs. The plasma concentrations of nicardipine on the 1st and 4th days of the administration are shown in FIG. 5.

TEST EXAMPLE 5

Figure 6:
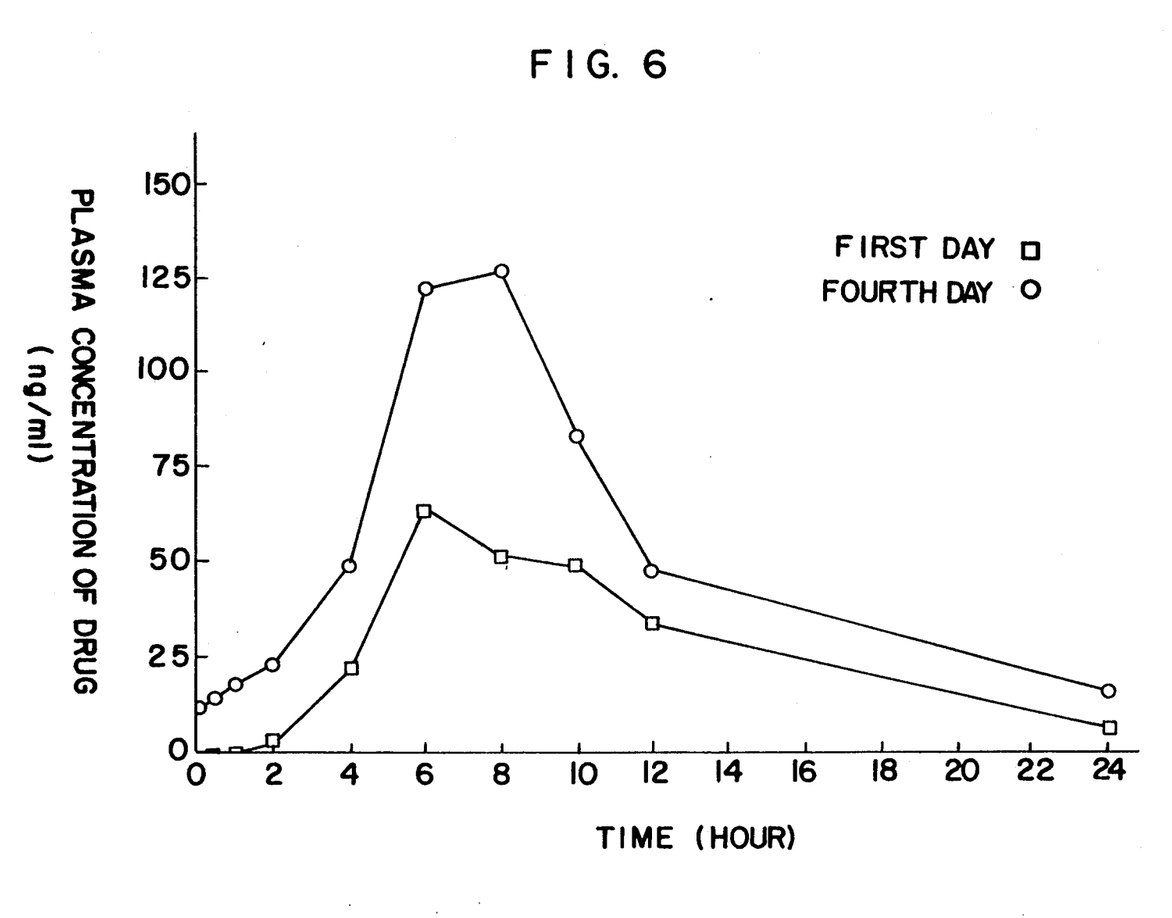
FIG. 6 shows the result of Test Example 5.

A long acting pharmaceutical preparation containing 180 mg of nicardipine hydrochloride prepared by Example 4 was administered once daily for four days to six male beagle dogs. The plasma concentrations of nicardipine on the 1st and 4th days of the administration are shown in FIG. 6.

TEST EXAMPLE 6

Figure 7:
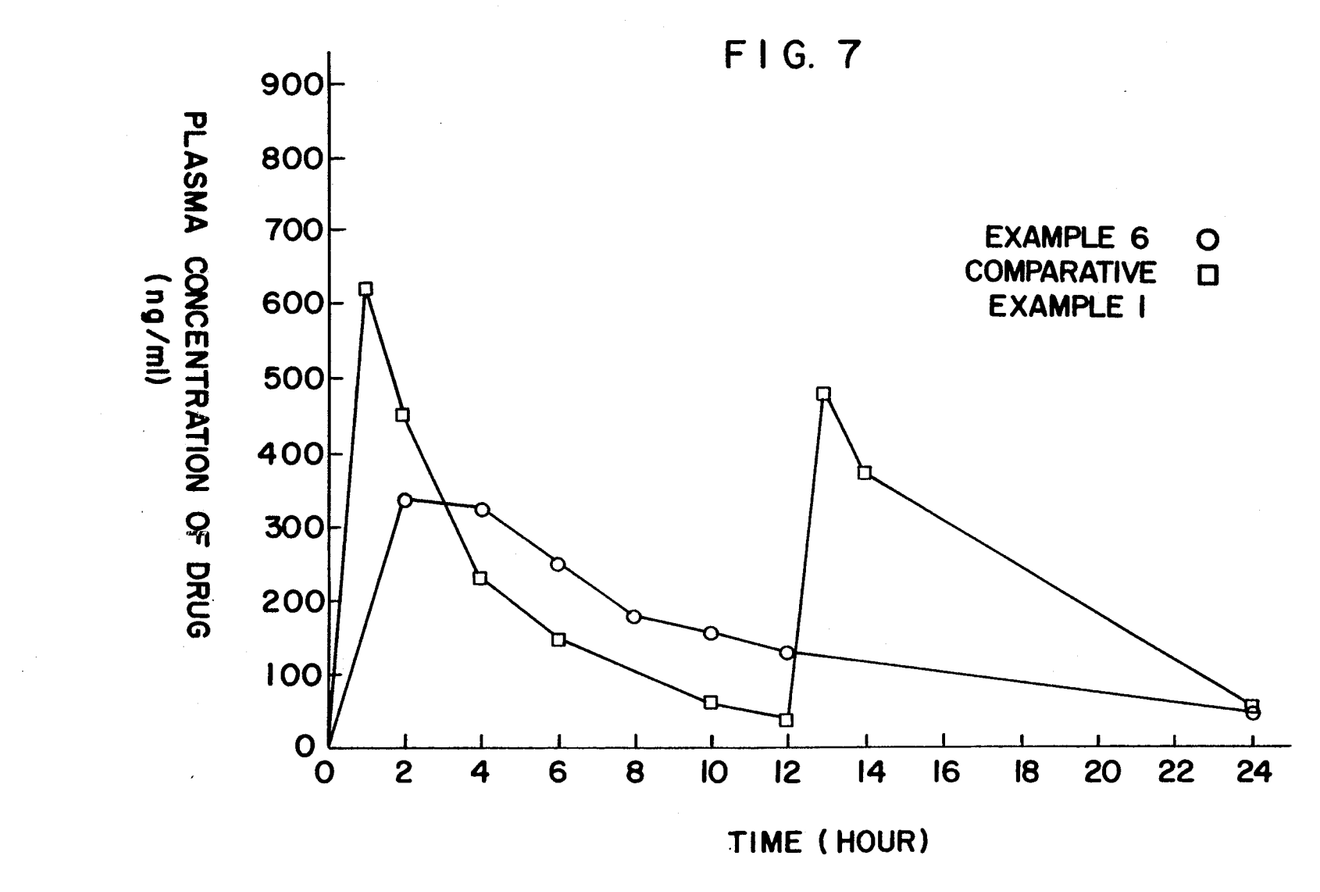
FIG. 7 shows the result of Test Example 6.

A long pharmaceutical preparation containing 100 mg of amosulalol hydrochloride prepared by Example 6 was administered once daily and one control tablet prepared by comparative example 1 containing 50 mg of amosulalol hydrochloride was administered twice daily to male beagle dogs. After administration, blood was drawn at predetermined intervals and the plasma concentrations of amusulalol were determined and compared. The results are shown in FIG. 7.

The conventional pharmaceutical preparation showed a rapid elevation of plasma concentration, while the preparation produced by Example 6 of the present invention showed a good slow releasing plasma concentration pattern.

EXAMPLES

The present invention is explained further in detail by the following Examples; however, the invention is not limited by these Examples.

Preparations of enteric granules (semi-long lasting pharmaceutical preparation) and gastric juice-soluble granules are shown as reference examples. Preparation of conventional tablets of amosulalol hydrochloride is shown as a comparative example.

REFERENCE EXAMPLE 1.

Five hundred gram of Nonparell 103 was coated with 2.6 kg of methanol : methylene chloride mixed solution (1 : 1 w/w) containing 200 g of niccardipine hydrochloride, 275 g of hydroxypropylmethylcellulose, 25 g of Macrogol 6000 and 20 g of Macrogol 400 by fluidized coating and dried to give round shaped gastric juice soluble granules.

REFERENCE EXAMPLE 2

Five hundred gram of Nonparell 103 was coated with 3.0 kg of methanol : methylene chloride mixed solution (1 : 1 w/w) containing 200 g of nicardipine hydrochloride, 200 g of Eudragit L100 and 50 g of Polysolvate 80 by fluidized coating to give round shaped granules. The dried 500 g of granules were further coated with 200 g a mixed solution of methanol : methylene chloride (1 : 1 w/w) containing 18.2 g of Eudragit RS 100L and 1.8 g of Macrogol 400 and dried to give enteric granules.

COMPARATIVE EXAMPLE 1

One hundred gram of amosulalol hydrochloride, 800 g of lactose and 200 g of corn starch were thoroughly mixed and an aqueous solution of 34 g of hydroxypropylcellulose was added and granules were prepared. The obtained granules were dried and tabletted by conventional tablet machine with the addition of 60 g of carboxymethylcellulose calcium and 6g of magnesium stearate.

EXAMPLE 1

Six hundred and thirty gram of Nonpareil 103 was coated with 3.3 kg of methanol : methylene chloride mixed solution (1 : 1 w/w) containing 400 g of nicardipine hydrochloride, 200 g of Eudragit L100 and 60 of Polysolvate 80 by fluidized coating and dried to solve round shaped granules. The dried 600 g of granules were coated by fluidized coating with 420 g of a mixed solution of methanol : methylene chloride (1 : 1 w/w) containing 30.0 g of Eudragit RS 100, 5.0 g of Eudragit S100, 5.0 g of Eudragit L100 and 2.0 g of Macrogol 400 to form a drug release control film. The coated granules were dried at 40° C. for four hours and filled into capsules in conventional manner.

EXAMPLE 2

Five hundred gram of amosulalol hydrochloride, 580 g of lactose and 1,020 g of crystalline cellulose were mixed, 2.0 kg of 15% citric acid aqueous solution was added and the mixture was kneaded. The kneaded mixture was granulated, rounded and dried to give granules containing amosulalol. Five hundred gram of the granules were coated with 350 g of a mixed solution of methanol : methylene chloride (1 : 1 w/w) containing 22.2 g of Eudragit RS100, 5.5 g of Eudragit S100, 5.5 g of Eudragit L100 and 1.8 g of Macrogol 400 to form a drug release control film, dried at 40° C. for four hours, and filled into capsules in conventional manner.

EXAMPLE 3

Granules prepared by Example 1 and reference examples 1 and 2 were mixed in a ratio of 4 : 1 : 5 of the main component (drug) and transferred into capsules to give a capsule preparation.

EXAMPLE 4

Granules prepared by Example 1 and reference example 2 were mixed in a ratio of 4 : 5 of the main component (drug) and transferred into capsules to give a capsule preparation.

EXAMPLE 5

Granules prepared by Example 1 and Reference Examples 1 and 2 were mixed in a ratio of 6 : 1 : 2 of the main component (drug) and filled into capsules to give a capsule preparation.

EXAMPLE 6

Five hundred gram of amosulalol hydrochloride, 580 g of lactose and 1,020 g of crystalline cellulose were mixed, 2.0 kg aqueous of 15% citric acid solution was added and the mixture was kneaded. The kneaded mixture was granulated, rounded and dried to give granules containing amosulalol.

Five hundred gram of the granules were coated by fluidized coating method with 400 of mixed solution of methanol methylene chloride (1 : 1 w/w) containing 24.5 of Eudragit RS 100, 8.2 of Eudragit RL100 (novel name RS100L) 4.1 g of Eudragit S100 1.6g of Eudragit L100 and 1.6g of Macrogol 400 to form a drug release control film, dried at 40° C. for four hours, and filled into capsules in conventional manner

We claim:

1. A drug release control composition for pharmaceutical formulations, the composition containing
   60–85 parts by weight of copolymer of ethyl acrylate, methyl methacrylate and trimethylammonioethyl methacrylate chloride in a molar ratio of 1 : 2 : 0.1; and a total of 15–40 parts by weight a component of and a component wherein
   is a copolymer of methyl methacrylate and methacrylic acid in a molar ratio of 1 : 1 and
   is a copolymer of methyl methacrylate and methacrylic acid in a molar ratio of 2 : 1; and optionally
   a copolymer of ethyl acrylate, methyl methacrylate and trimethylammonioethyl methacrylate chloride in a molar ratio of 1 : 2 : 0.2, the amount of being 0–30 parts by weight per 100 parts of the combined weight of.

* * * * *

UNITED STATES PATENT AND TRADEMARK OFFICE
CERTIFICATE OF CORRECTION

PATENT NO. : 5,028,664

DATED : July 2, 1991

INVENTOR(S) : Tadayoshi Ohmura

It is certified that error appears in the above-identified patent and that said Letters Patent is hereby corrected as shown below:

Column 8, line 54: "60-85" should read --(a) 60-85-- line 57: "weight a component" should read --weight of a component (b)-- line 58: "of and a component" should read --and a component (c)-- line 59: "is a copolymer" should read --(b) is a copolymer-- line 61: "is a copolymer" should read --(c) is a copolymer-- line 63: "a copolymer" should read --(d) a copolymer--

Signed and Sealed this

Fifth Day of January, 1993

*Attest:*

DOUGLAS B. COMER

*Attesting Officer*  *Acting Commissioner of Patents and Trademarks*